United States Patent
Cortella et al.

(10) Patent No.: US 6,277,096 B1
(45) Date of Patent: Aug. 21, 2001

(54) DIGITAL FLUID DELIVERY AND ASPIRATION APPARATUS WITH MECHANICAL DE-AMPLIFIER

(75) Inventors: Julian M. Cortella, Alameda; Carl C.T. Wang, Oakland, both of CA (US)

(73) Assignee: Medical Instrument Development Laboratories, Inc., San Leandro, CA (US)

(*) Notice: Subject to any disclaimer, the term of this patent is extended or adjusted under 35 U.S.C. 154(b) by 0 days.

(21) Appl. No.: 09/592,642

(22) Filed: Jun. 13, 2000

Related U.S. Application Data (62) Division of application No. 08/940,189, filed on Sep. 30, 1997, now Pat. No. 6,102,895.

(51) Int. Cl.[7] .................................................. A61M 37/00
(52) U.S. Cl. ........................................... 604/143; 604/209
(58) Field of Search ................................... 604/207–209, 604/218, 224, 131, 141, 140, 143, 147, 154

(56) References Cited

U.S. PATENT DOCUMENTS

| | | |
|---|---|---|
| 3,517,668 | 6/1970 | Brickson . |
| 4,589,870 | 5/1986 | Citrin et al. . |
| 4,659,327 | 4/1987 | Bennett et al. . |
| 4,865,591 | 9/1989 | Sams . |
| 5,017,190 | 5/1991 | Simon et al. . |
| 5,336,201 | 8/1994 | von der Decken . |
| 5,354,268 | 10/1994 | Peterson et al. . |
| 5,370,630 | 12/1994 | Smidebush et al. . |
| 5,520,652 | 5/1996 | Peterson . |
| 6,102,895 | 8/2000 | Cortella et al. . |

FOREIGN PATENT DOCUMENTS

12528    7/1903   (DE) .

*Primary Examiner*—Sharon Kennedy
*Assistant Examiner*—Catherine Serke
(74) *Attorney, Agent, or Firm*—Godfrey B. Kahn, S.C.; William K. Baxter

(57) ABSTRACT

A digital fluid delivery and aspiration apparatus with a mechanical de-amplifier for the delivery or removal of discrete volumes of fluidic material from a surgical site. The apparatus has a syringe with a plunger designed to be powered by a pneumatic air supply system. A ratcheting mechanism attached to a pneumatic piston by a mechanical linkage causes the plunger of the syringe to inject discrete doses of the fluidic material into the surgical site or remove discrete amounts of fluidic material from the surgical site. The mechanical linkage increases the force provided to the plunger by the movement of the piston and also de-amplifies the movement of the piston into a lesser movement of the plunger. Adjusting the waveform of the pneumatic air supply, coupled with the mechanical de-amplification of the movement of the pneumatic piston, reduces the jetting of the fluidic material being delivered, and allows the delivery or removal of precise volumes of fluidic material from the surgical site at precise rates without damaging the tissue into which or from which the fluidic material is being delivered or removed. The irrigation and aspiration features may be incorporated into one device.

13 Claims, 9 Drawing Sheets

FIG_2

FIG_11

FIG_12

FIG_13 PRIOR ART

FIG_14

FIG_15

FIG_17

FIG_16

FIG_22

DIGITAL FLUID DELIVERY AND ASPIRATION APPARATUS WITH MECHANICAL DE-AMPLIFIER

CROSS-REFERENCE TO RELATED APPLICATIONS

This application is a divisional of U.S. application Ser. No. 08/940,189, now U. S. Pat. No. 6,102,895, filed Sep. 30, 1997, issued Aug. 15, 2000.

FIELD OF THE INVENTION

This invention relates generally to devices for the delivery of fluidic material to, and the removal of fluidic material from, body tissue. More particularly, the present invention relates to pneumatically controlled devices capable of delivering or removing precise volumes of fluidic material at a selected site.

BACKGROUND OF THE INVENTION

The delivery or injection of fluidic materials to and removal of fluidic materials from a selected site may be performed in a number of different medical procedures. In the field of ophthalmology, for example, intraocular injections may be administered for many reasons. Some of these reasons include: (1) the injection of antibodies to treat endothalmitis or prevent its onset; (2) the injection of Transforming Growth Factor Beta (TGFB) or other growth factors to treat macular disorders; (3) the injection of Tissue Plasminogen Activator (tPA) into the subretinal space to dissolve blood clots; (4) the injection of liquids and gases into the subretinal space to facilitate subretinal surgery; (5) the injection of viscoelastic substances to dissect preretinal membranes; and (6) the injection of gases into the vitreous cavity for pneumatic retinal pexy.

When injections are administered to delicate tissue, e.g., intraocular injections, the surgeon must control the following: injection rate, total volume administered, and location of the injected substance. Similar concerns exist for aspiration of fluids from delicate tissues. The case of viscodissection is described below to illustrate these requirements.

Viscodissection is a technique where preretinal membranes are hydraulically separated from the retina using a viscoelastic substance. This substance, typically sodium hyaluranate, is delivered between the preretinal membrane and the retina using a syringe and a small gauge bent needle. The fluid creates a working space underneath the retina. Many surgeons find it difficult to hold the needle tip steady while injecting the fluid and inadvertent motion of the needle can cause damage to the retina or other surrounding tissues. Further, injecting too much fluid between the preretinal membrane and the retina, or injecting the fluid too fast, can also cause retinal damage which could lead to retinal detachment. Similarly, aspiration of unwanted fluid from these delicate tissues requires steady and measured suction.

Figure 13:
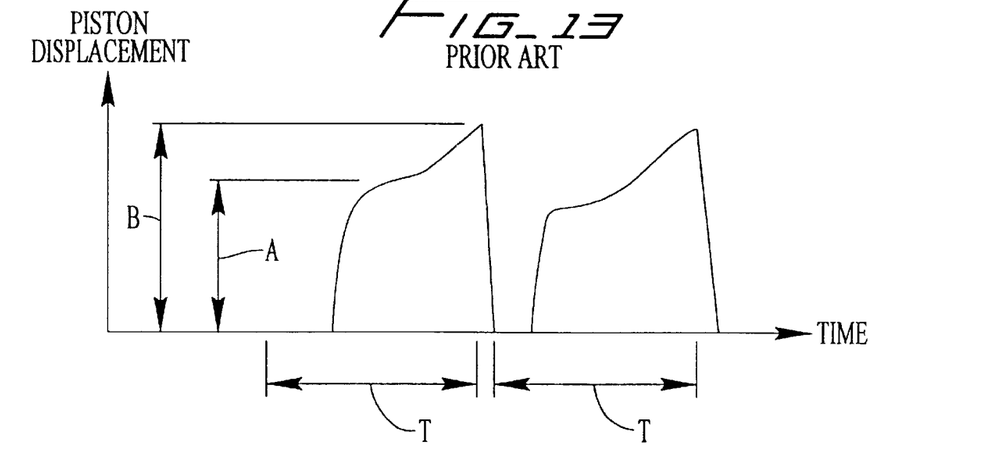
FIG. 13 is a graphical diagram showing a piston displacement v. time curve typical of existing pneumatic injectors.

There are some devices which facilitate the delivery of fluidic materials to delicate tissue. For example, U.S. Pat. No. 5,370,630 discloses a device that uses pneumatic energy to cause the injection of fluidic material into body tissue. The plunger of this device is driven by pneumatic pressure instead of finger pressure, thereby allowing the surgeon to better control the injection rate, volume, and location. A number of other syringe adapters and pneumatic pressure sources are currently available. Such devices typically have a piston displacement v. time curve as shown in FIG. 13.

While more effective than manual instruments, existing pneumatic fluid delivery devices often cannot meet the requirements of the surgeons for precision because they cannot control the "jetting" of material emitted from the needle, require a relatively high amount of pneumatic pressure to operate, and cannot be precisely controlled for very low doses. "Jetting," or turbulent flow of the fluidic material, occurs when the fluid emitted through the hole in the needle is forced out under relatively high pressure by a rapidly accelerating plunger motion. Jetting is undesirable because it may damage the tissue to which the fluidic material is being delivered. Similarly, existing aspiration devices do not meet the needs of surgeons for aspiration of delicate tissue because they do not offer adequate control of the suction force in strength, location, and volume.

The major deficiencies of existing devices are caused by internal friction. As with any dynamic system, friction is present in devices designed to deliver fluids. With air cylinders, as in existing injectors, friction due to o-rings rubbing against the walls of the cylinder can be very difficult to control. All o-ring type piston-cylinder assemblies have an inherent problem with initial static friction created by at least two sources. One is static friction due to material properties; the other is commonly referred to as "stiction." Stiction is the frictional force due to a compression of the o-ring incurred when the piston-cylinder assembly has been sitting unused for some time. The ideal control for injection is a constant velocity, linear displacement travel of the piston. In prior-art devices, the stiction and static friction in the air cylinder result in uncontrollable motion, which is illustrated in FIG. 13. As pressure is increased to initiate motion of the piston, initially nothing happens. Then, there is an almost instantaneous movement of the piston (from zero to a level indicated by reference numeral A) as the friction and stiction forces are overcome. This jump in motion results in the jetting of the fluid being delivered. This initial jump can be as much as 75% of the total stroke (reference numeral B) of the piston. Thus, no matter how well the delivered air supply is controlled, the result is a quick, pulse-like delivery of fluid and potential damage to the tissue into which the fluidic material is being injected.

Existing aspiration devices typically do not offer precise control of the rate and volume of fluid being aspirated and thus are not very useful around sensitive tissues. Specifically, current aspiration devices used in intraocular surgery, such as those used in vitrectomy procedures, use vacuum control. In such devices, the vacuum level is controlled, not the rate or volume of material aspirated. Aspiration devices typically used in cataract surgery suffer from several limitations. First, such devices cannot accurately remove fluids in the sub-microliter range and thus cannot be used around delicate tissue such as the retina. Second, such devices are flow-controlled rather than volume-controlled, that is, the surgeon can control the suction rate at which material is removed, but not the volume. Thus, existing devices cannot be used to remove a precise volume of material as may be required in surgeries such as the treatment of sub-retinal hemorrhages.

Accordingly, a need has arisen for a device capable of delivering and removing fluidic materials from delicate body tissue. Further, it would be desirable if the device could deliver a user-settable volume of fluid; deliver and remove fluids at a volume rate precisely controlled by the operator; allow the use of a relatively low pressure pneumatic source; reduce jetting of fluid emanating from the needle; and further minimize the risk of tissue damage that results from manually operated syringes, existing pneumatic syringes, and existing aspiration devices.

SUMMARY OF THE INVENTION

Therefore, it is an object of the present invention to provide a fluid delivery and aspiration apparatus that prevents the jetting of fluidic material through the hole in the end of the needle.

It is a further object of the present invention to provide a fluid delivery and aspiration apparatus that can deliver or remove precise volumes of fluidic material from a surgical or therapy site ("selected site").

It is an additional object of the present invention to provide a fluid delivery and aspiration apparatus that can deliver fluidic material to and remove fluidic material from a selected site at a precise rate and volume.

It is yet another object of the present invention to provide a fluid delivery and aspiration apparatus capable of delivering fluidic material to and removing fluidic material from a selected site without damaging delicate tissue.

The present invention provides the above-identified and many additional objects by providing a digital fluid delivery and aspiration apparatus with a mechanical de-amplifier wherein a pneumatically driven piston mechanically coupled to a plunger pushes the fluidic material out or sucks the fluid into a syringe at a rate and volume that can be precisely controlled.

The invention includes a syringe and housing. The syringe includes a barrel housing a plunger, teeth formed at least partially about the periphery of the plunger, the multiple teeth running along at least a portion of the length of the plunger. The plunger travels within and along the barrel to either force the fluidic material out of the barrel of the syringe or draw fluid into the barrel of the syringe depending on the direction of the motion of the plunger. The teeth on the plunger engage a ratcheting mechanism inside the housing to provide step-wise, or digital, control of the injection or aspiration rate and volume.

Figure 14:
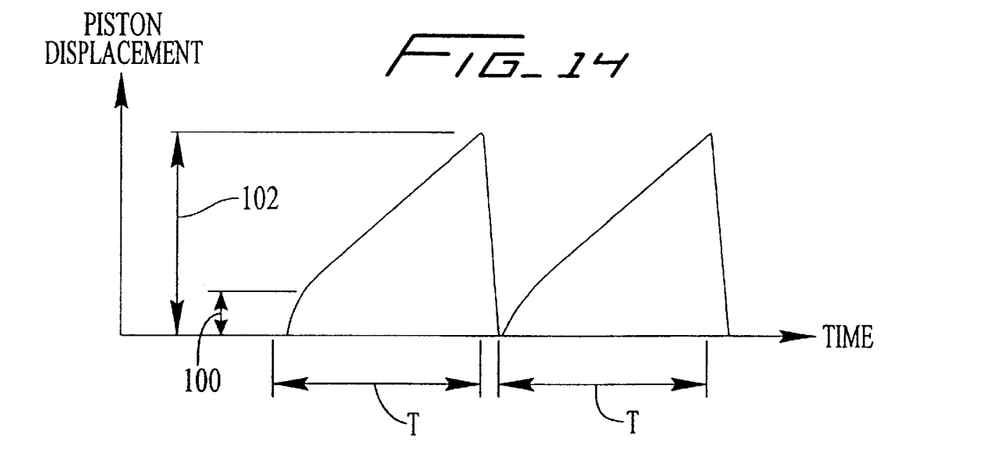
FIG. 14 is a graphical diagram showing the piston displacement v. time curve of the apparatus in accordance with the present invention.

The housing includes a base which provides a place to attach the syringe and a cap enclosing a piston, a mechanical linkage, and the ratcheting mechanism. The ratcheting mechanism engages the teeth on the plunger to move the plunger within the syringe. The ratcheting mechanism is connected to the mechanical linkage which is further connected to the pneumatically driven piston. When the apparatus is used to deliver fluid to a site, the piston is preferably biased toward the upper housing piece by a coil spring and is driven toward the base by an external pneumatic source capable of overcoming the spring's bias. This motion engages the mechanical linkage connected to the ratcheting mechanism. The motion of the piston, shown in the piston displacement v. time curve of FIG. 14, is thereby translated to a displacement of the plunger towards the end of the open syringe (thus, FIG. 14 also charts the plunger displacement). When the pneumatic source is removed, the bias of the spring returns the piston to its original position and a leaf spring retains the position of the syringe plunger and prevents it from returning to its original position as the ratcheting mechanism returns to its original position in anticipation of another cycle. As should be evident to one skilled in the art, a similar, but oppositely oriented device is used for aspiration. Furthermore, it should be evident that other biasing means including pneumatic or hydraulic force may be used to return the piston to its original position.

The use of mechanical linkage provides several distinct advantages over existing pneumatically driven injectors. First, the use of mechanical linkage to provide mechanical leverage to the ratcheting mechanism permits the use of much lower pressure than is required by existing systems. This allows the use of small, compact compressors or other air sources, resulting in overall cost and size reductions. Second, the use of the mechanical linkage results in a motion de-amplification. That is, for every unit of displacement the piston travels, the ratcheting mechanism, and hence the plunger, travels a shorter distance in a ratio equal to the leverage provided by the mechanical linkage. This permits much more precise control of the rate of the fluid delivery or removal because the acceleration and speed of the plunger is reduced. Third, the use of mechanical linkage to provide motion de-amplification also results in a decreased influence of friction on the control of the plunger, resulting in a linearly displaced, constant velocity injection or aspiration. In existing pneumatic injectors, a much greater percentage of the plunger motion is adversely affected by the jump in the plunger after the friction in the system had been overcome by the air pressure. (See FIG. 13). Finally, the mechanical linkage allows the use of a stronger return spring or other biasing means, thereby further reducing the adverse effects of friction on the motion of the plunger.

The forces opposing the motion of the piston are friction and the biasing force. The biasing force is much more controllable than the friction and by increasing the biasing force, the friction resistance force represents a much smaller component of the overall resistance force than in existing pneumatic injectors. Thus, the ability to precisely control the rate and volume of fluidic material delivered is greatly increased and tissue damage from jetting is reduced in the present invention. Similarly, the ability to control the plunger motion allows the surgeon to precisely control the rate and volume of fluidic material aspirated from a site because the device is volume-controlled rather than vacuum controlled.

In the preferred embodiment, when it is necessary to fill the syringe with fluidic material for delivery or empty fluidic material that has been aspirated, the plunger can be rotated to disengage the teeth from the ratcheting mechanism. In this position, the plunger rod can be moved freely in either direction by manually pulling or pushing the plunger as in the operation of a standard syringe. In an alternative embodiment, the syringe is filled or emptied using the pneumatic control.

Figure 15:
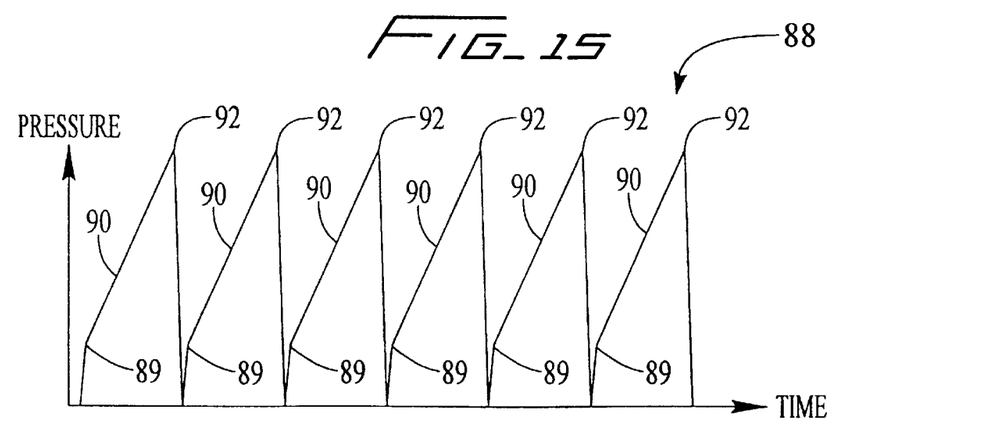
FIG. 15 is a graphical diagram of the pulse train and wave form of the pressurized air used with the apparatus in accordance with the present invention.

The external pneumatic actuation force is supplied as a series of controlled pulses. For each pulse delivered to the apparatus, the plunger rod travels one unit of length, the length of that unit being determined by the distance between the edges of the teeth on the plunger. Thus, the distance traveled is independent of the externally supplied pressure or the fluidic material being delivered or removed. Existing pneumatically driven syringes are typically powered by a series of sharp pulses of compressed air. This rapid, pulsing excitation of the piston contributes to undesirable jetting or turbulent flow of fluid from the tip of the syringe needle. Existing aspiration devices typically provide a constant level of suction, and control of volume aspirated is difficult to achieve. The present invention uses a pulse train having a waveform substantially as shown in FIG. 15. The air pressure is precisely controlled to reduce the occurrence of jetting during delivery. There is a small, initial jump to a low pressure which has the effect of overcoming the friction in the system. Beyond the low pressure level, smoothly increasing pressure to a maximum level results in the smooth plunger motion. In exciting the piston in this fashion, the acceleration of the plunger is reduced, thereby reducing jetting during delivery. Although pneumatic control of the piston is preferred, it should be understood by those of skill in the art of the invention that hydraulically driven pistons could be used. Accordingly, as used herein the terms "pneumatically," "air pressure," "pneumatic," and other gaseous references should be read and interpreted to include liquids and hydraulic systems. Furthermore, it should be evident that the piston may be sealed against the housing by means other than an O-ring. One such design incorporates a rolling diaphragm connected to the piston.

These are just some of the features and advantages of the present invention. Many others will become apparent by reference to the detailed description of the invention taken in combination with the accompanying drawings. It should be noted that while the detailed description frequently refers to use of the invention as a fluid delivery instrument, the invention may be used for aspiration by reversing the direction of stepwise plunger control, and a device in accordance with the invention may incorporate both irrigation and aspiration in the same device.

DETAILED DESCRIPTION OF THE PREFERRED EMBODIMENTS

Figure 1:
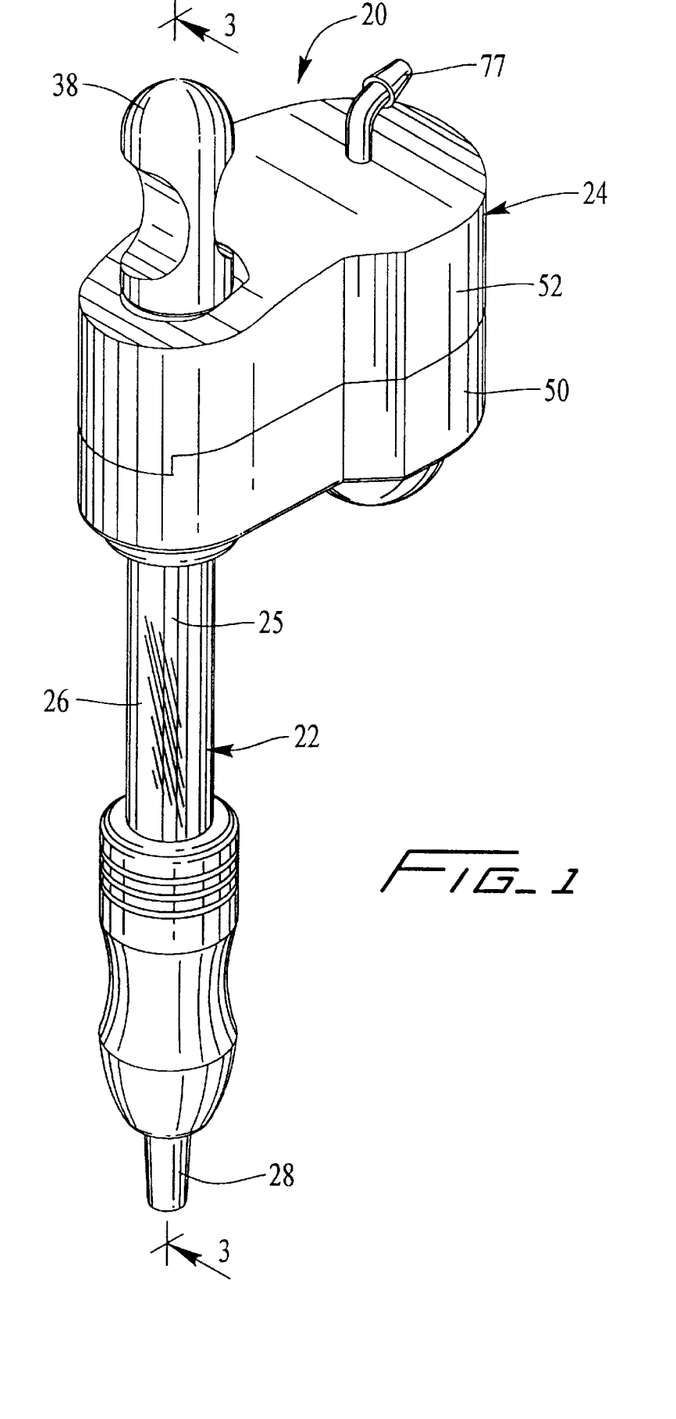
FIG. 1 is a perspective view of a digital fluid delivery and aspiration apparatus with a mechanical de-amplifier constructed in accordance with a preferred embodiment of the present invention.

As illustrated in FIG. 1, a digital fluid delivery and aspiration apparatus 20 includes a syringe 22 and a housing 24 with a plunger 25 inserted through both the syringe 22 and the housing 24. While the following description is directed mainly toward the delivery apparatus embodiment of the invention, it should be understood by one skilled in the art that the aspiration apparatus embodiment is constructed to provide digital control of the plunger 25 in the opposite direction as the fluid delivery apparatus embodiment. Furthermore, as described below, the aspiration apparatus embodiment and the fluid delivery apparatus embodiment may be combined in one apparatus.

Figure 2:
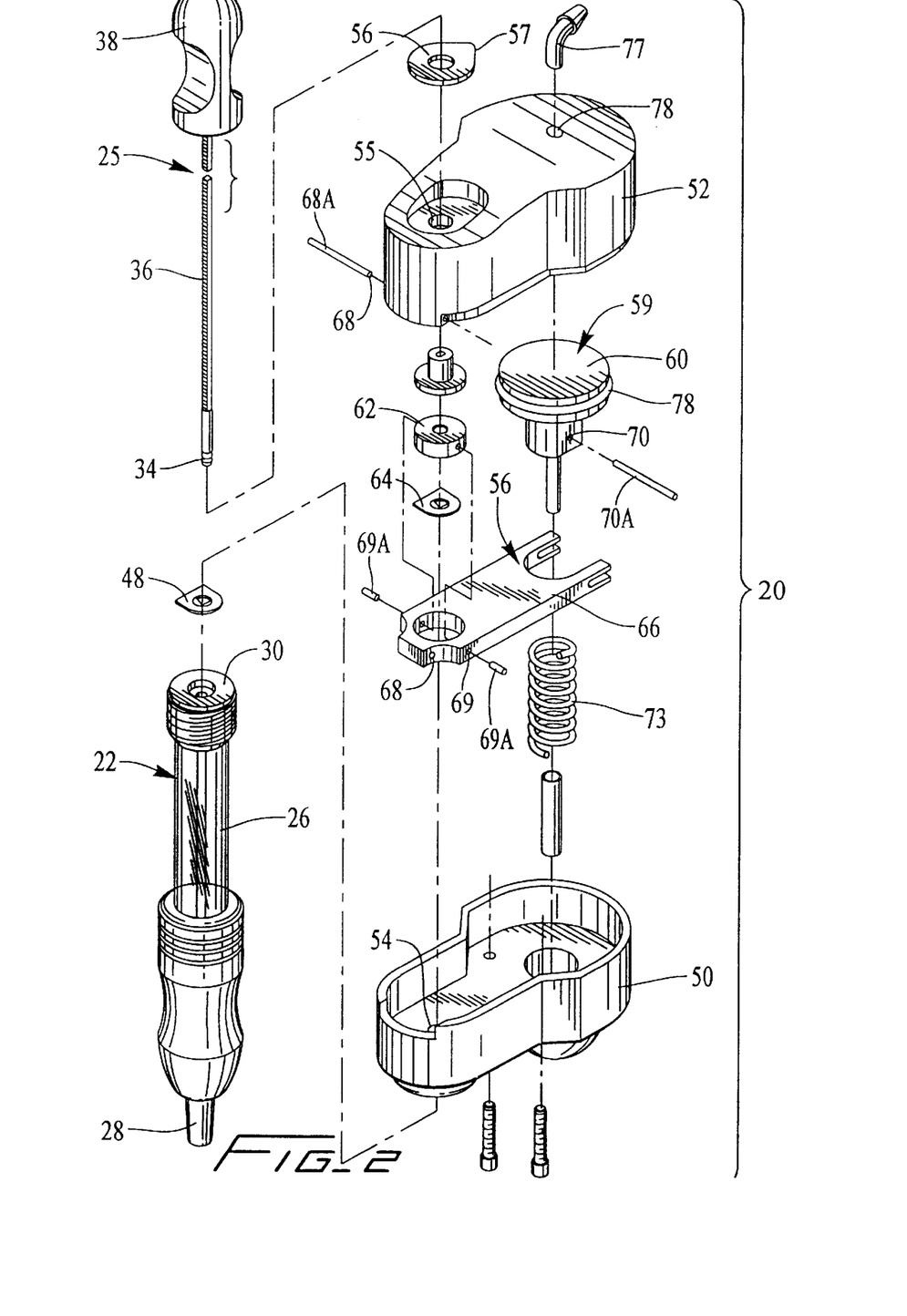
FIG. 2 is a perspective exploded view of the digital fluid delivery and aspiration apparatus with a mechanical de-amplifier in accordance with a preferred embodiment of the present invention.
Figures 11, 12:
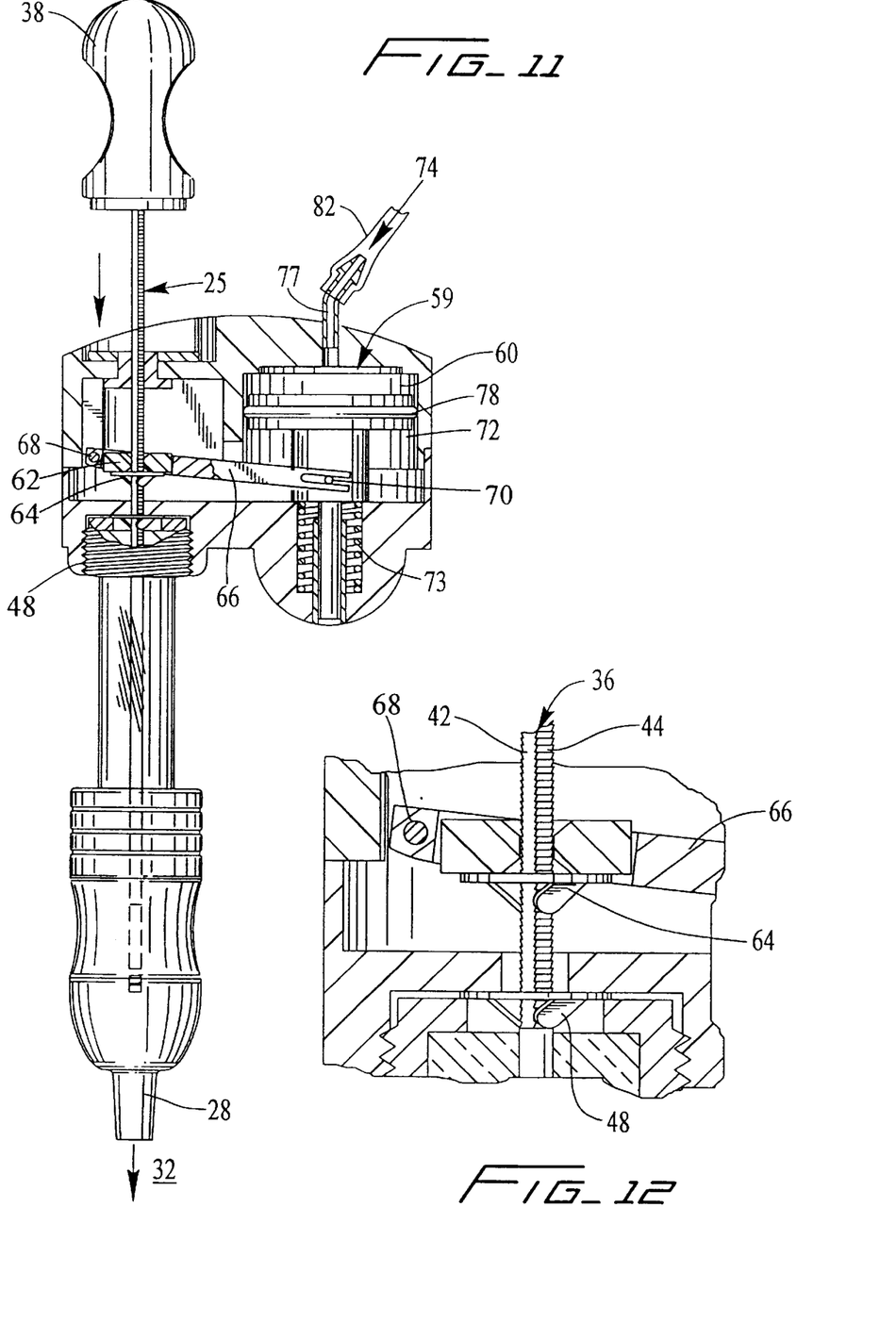
FIG. 11 is a side elevational view, partially in cross-section, of the apparatus in accordance with the present invention reflecting movement of the plunger such that fluidic material is discharged from the barrel of the syringe.
FIG. 12 is a side elevational view of the cross-section of FIG. 11, shown in greater detail.

As shown in FIG. 2, the syringe 22 is similar to a standard syringe in that it has a hollow barrel 26 having a needle receiving end 28 and a plunger receiving end 30. The plunger receiving end 30 is attached to the housing 24 and receives the plunger 25 while a needle (not shown) may be attached to the needle receiving end 28. The plunger 25 can travel the length of the barrel 26 to either force fluidic material 32 out of the barrel 26 or draw fluidic material 32 into the barrel 26 depending on the direction of the motion of the plunger 25. To accomplish this, the plunger 25 is substantially radially sealed against the interior of the barrel 26. In a preferred embodiment, this is accomplished by use of a fluidic material engaging head 34 that radially seals the plunger 25 against the interior of the barrel 26. The fluidic material engaging head 34 forces the fluidic material 32 out of the needle receiving end 28 of the barrel 26 when the plunger 25 moves through the barrel 26 from the plunger receiving end 30 toward the needle receiving end 28. (FIG. 11). The fluidic material engaging head 34 creates a vacuum that draws fluidic material 32 into the barrel 26 when the plunger 25 moves through the barrel from the needle receiving end 28 toward the plunger receiving end 30. (FIG. 7).

Figures 3, 4, 5, 6:
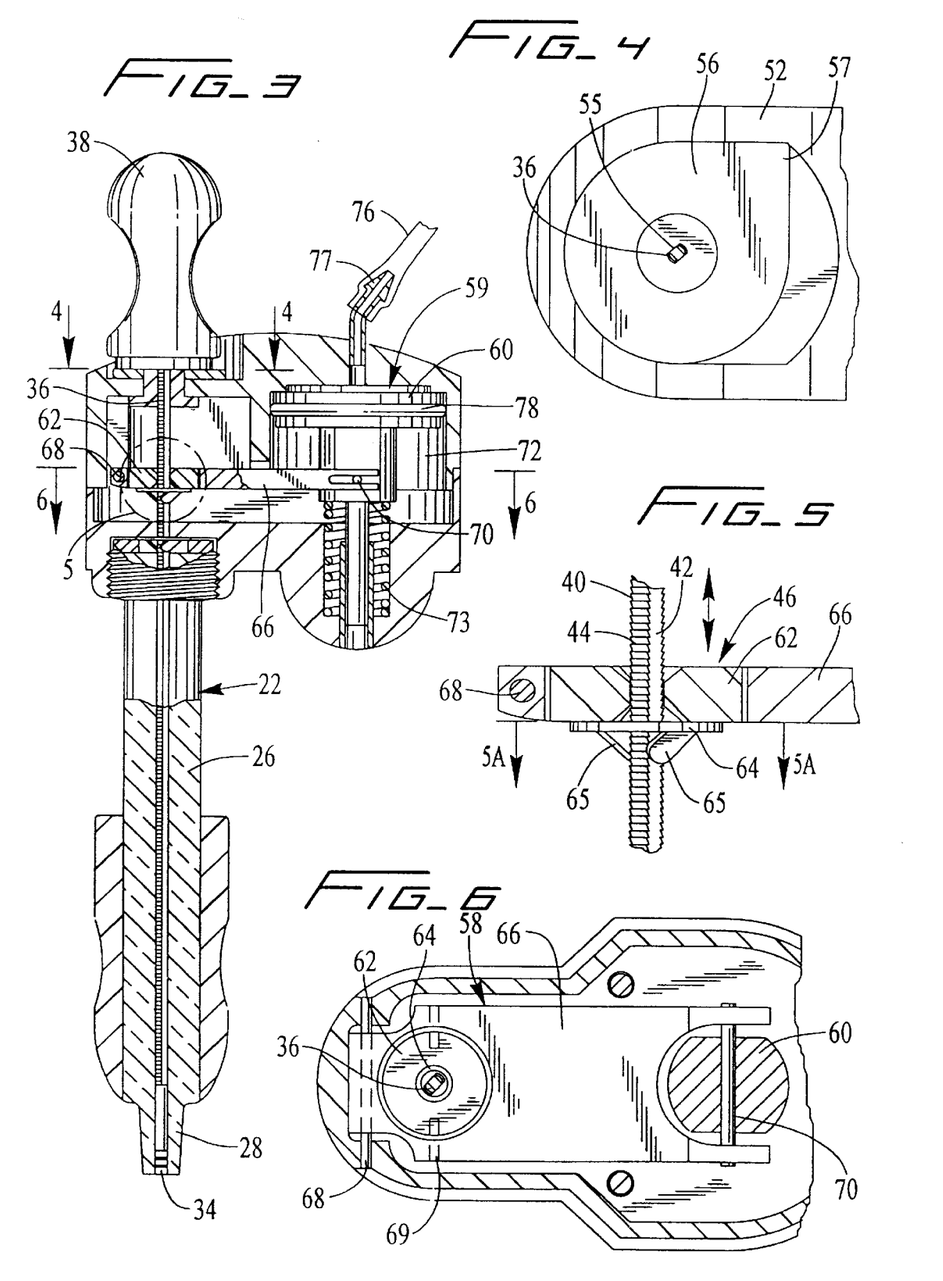
FIG. 3 is a side elevational view, shown mostly in cross-section, of the apparatus as shown in FIG. 1, taken generally along the plane 3—3.
FIG. 4 is a partial top plan view of the apparatus shown in FIG. 1, having the lever arm oriented such that the teeth of the plunger do not engage the ratchet spring.
FIG. 5 is an enlarged detail view a portion of the cross section shown in FIG. 3.
FIG. 6 is a top plan view, partially in cross-section, of the apparatus as shown in FIG. 3 taken generally along the line 6—6.

The plunger 25 includes a shaft 36 having the fluidic material engaging head 34 on one end and a plunger control 38 on the opposite end. The shaft 36 is provided with a number of teeth 44 on its periphery and running along most of its length. As shown in cross-section in FIGS. 5A and 10, in this embodiment, the shaft 36 has two toothed faces 40, which are shown with curved outer surfaces in this embodiment, and two toothless faces 42, shown with flat surfaces, along its length. The teeth 44 on the toothed or curved faces 40 are oriented axially toward the plunger control 38 end of the shaft 36. The plunger 25 can rotate about its longitudinal axis within the barrel 26 and the housing 24. (FIG. 9). Such rotation allows either the curved faces 40 having teeth 44 (FIGS. 9 and 10) or the toothless or flat faces 40 (FIGS. 5 and 5A) of the shaft 36 to be oriented toward a ratcheting mechanism 46 in the housing 24.

When the toothed faces 40 are oriented toward a ratcheting mechanism 46 disposed in the housing 24 (FIGS. 9 and 10), the interaction of the teeth 44 and ratcheting mechanism 46 provides stepwise, in a sense digital, control of the travel of the plunger 25 from the plunger receiving end 30 of the barrel 26 to the needle receiving end 28 of the barrel 26. The ratcheting mechanism 46 provides the stepwise control only in this direction because the plunger 25 is prevented from sliding toward the plunger receiving end 30 of the barrel 26 by a pair of pawls 47 integrally formed with a leaf spring 48 in the housing 24 engaging the teeth 44, one pawl on each side of the shaft 36, thus preventing fluidic material 32 from being reintroduced to the barrel 26 after it has been forced out through the needle receiving end 28. Of course, the orientation of the ratcheting parts, including teeth 44 and ratcheting mechanism 46, is reversed for the aspiration apparatus embodiment of the present invention.

Figures 5A, 7, 8, 9, 10:
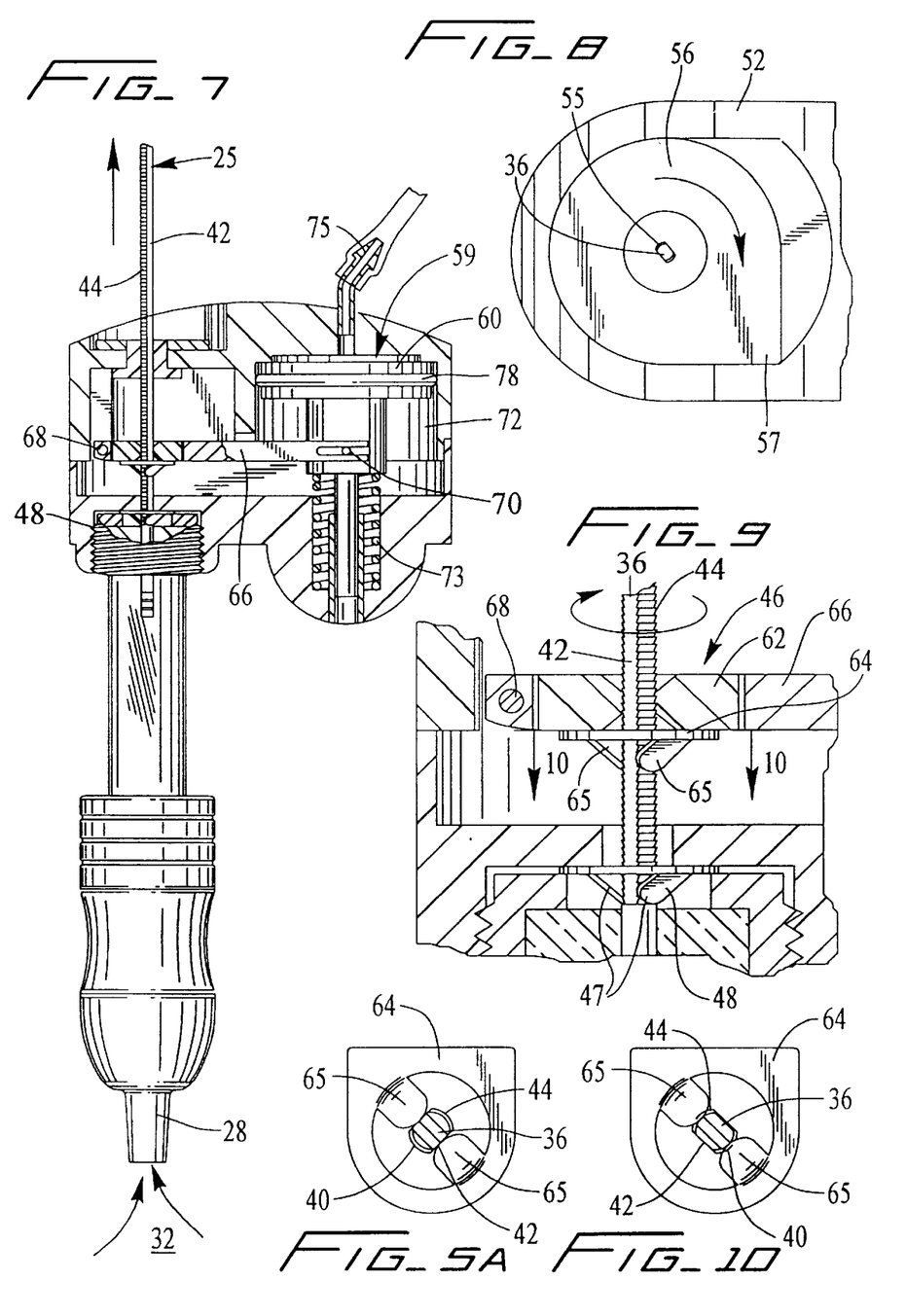
FIG. 5A is a partial top plan view, shown partially in cross-section, of the apparatus as shown in FIG. 5 taken generally along the line 5A—5A in FIG. 5.
FIG. 7 is a side elevational view, partially in cross-section, of the apparatus as shown in FIG. 3, reflecting movement of the plunger such that fluidic material is drawn into the barrel of the syringe prior to delivery to a surgical site.
FIG. 8 is a partial top plan view of the apparatus shown in FIG. 7 having the lever arm oriented such that the teeth of the plunger engage the ratchet spring.
FIG. 9 is a side elevational view, partially in cross-section, of the apparatus shown in FIG. 7 having the plunger oriented such that the teeth engage the ratchet spring.
FIG. 10 is a top plan view, partially in cross-section, of the apparatus as shown in FIG. 5 taken generally along the line 10—10 in FIG. 9.

As illustrated in FIG. 7, when the flat faces 42 are oriented toward the ratcheting mechanism 46 (FIG. 5A), the plunger 25 is free to slide within the barrel 26 and the housing 24 either toward or away from the needle receiving end 28 of the barrel 26 as manipulated by the operator using the plunger control 38. This orientation is most useful in the fluid delivery apparatus embodiment when loading the barrel 26 with fluidic material 32 for delivery by moving the plunger 25 within the barrel 26 from the needle receiving end 28 toward the plunger receiving end 30. And in the aspiration apparatus embodiment, this orientation is most useful when emptying the barrel 26 of aspirated material 32 by moving the plunger 25 within the barrel 26 from the plunger receiving end 30 toward the needle receiving end 28.

The housing 24 includes a base 50 and a cap 52 (FIG. 2). The syringe 22 attaches to the base 50 at a base plunger hole 54 where the syringe 22 receives the plunger 25 after the plunger 25 has been inserted through the cap 52 and the base 50. The leaf spring 48 is positioned within the base 50 so that the pawls 47 engage the teeth 44 on the curved faces 40 of the shaft 36 such that the plunger 25 cannot be withdrawn from the barrel 26 without rotating the shaft 36 to a position where the flat faces 42 are oriented toward the pawls, so that the teeth are not engaged. When the flat faces 42 are so oriented, the plunger 25 can then move freely within the length of the barrel 26. Because it is advantageous to have a visual indication of whether the plunger 25 can move freely within the barrel 26, a plunger orientation indicator 56 is positioned on top of the cap 52, which rotates with the plunger. Indicator 56 includes a pointed portion 57 capable of indicating whether the curved faces 40 (FIG. 4) or the flat faces 42 (FIG. 8) are oriented toward the pawls 47.

Also positioned within the housing 24 is the ratcheting mechanism 46 which engages the teeth 44 to provide digital control of the plunger 25. Mechanical linkage 58 which moves the ratcheting mechanism 46 and a fluid power actuator 59, including a pneumatic piston 60, which drives the mechanical linkage 58 are also positioned within the housing 24.

The ratcheting mechanism 46 may be any combination of springs, levers, or other assemblies capable of digitally moving the plunger 25 within the barrel 26 toward the needle receiving end 28. In the preferred embodiment, the ratcheting mechanism 46 comprises a spring guide 62 and a ratchet spring 64 integrally formed with a pair of pawls 65, similar to the pawls 47 and leaf spring 48, in the housing 24. The spring guide 62 positions the ratchet spring 64 around the shaft 36 of the plunger 25 such that the pawls 65 engage the teeth 44 on the curved faces 40 when the plunger 25 is oriented such that the pawls 47 also engage the teeth 44. Thus, as the spring guide 62 and ratchet spring 64 are caused by the mechanical linkage 58 to move toward the needle receiving end 28 of the barrel 26, pawls 65 engage the teeth 44 and cause the plunger 25 to move toward the needle receiving end 28 of the barrel 26. When, however, the mechanical linkage 58 causes the spring guide 62 and ratchet spring 64 to move toward the plunger receiving end 30 of the barrel 26, the pawls 47 retain the plunger 25 in its new position and pawls 65 slide to engage another set of the teeth 44 to be positioned to repeat the digital movement of the plunger 25. The operation is performed in the opposite direction when the invention is configured to aspirate fluids.

The mechanical linkage 58 connects the ratcheting mechanism 46 to the fluid power actuator 59. The mechanical linkage 58 may be a combination of levers, pivot points, and other assemblies capable of allowing the use of lower pressure air to power the piston 60, capable of permitting more precise control of the rate of fluid delivery by reducing the speed and acceleration of the plunger's 25 movement, and capable of decreasing the influence of friction on the control of the plunger 25. In the preferred embodiment, the mechanical linkage 58 comprises a lever arm 66 connected to the base 50, spring guide 62, and piston 60 at three pivot points 68 (fulcrum), 69 (load), and 70 (effort) respectively. Pivot pins 68A, 69A, and 70A pivotably connect the lever arm 66 to the three pivot points 68, 69, and 70 respectively. In this embodiment, the lever arm 66 is a second class lever with the fulcrum 68 at the edge of the base 50, the load 69 at the spring guide 62, and the effort 70 at the piston 60. Thus, because the piston 60 (effort) is much further from the base pivot point 68 (fulcrum) than the spring guide 62 (load), the force needed to move the spring guide 62 is substantially reduced. Thus, when the piston 60 moves a distance, the ratcheting mechanism 46 moves a related distance and when a force moves the piston 60, a related force is provided to move the ratcheting mechanism 46. In the preferred embodiment, for every five units of displacement of the piston 60, the ratcheting mechanism 46 moves one unit of length and the force provided to move the ratcheting mechanism 46 is approximately five times more than the force required to move the piston 60, thereby enabling the use of much lower pneumatic pressure to drive the motion of the piston 60.

The piston 60 is positioned in a chamber 72 formed within the housing 24 and is biased, such as by a spring 73, toward the end of the chamber 72 formed by the cap 52. Compressed air 74 from a pneumatic air supply 75 (FIG. 16) may be introduced into the chamber 72 through an air tube 76 to a hollow tubing barb 77 inserted into an air hole 78 in the cap 52 leading into the chamber 72. The introduction of compressed air 74 into the chamber 72 forces piston 60 to move against the bias of the spring 73 causing the mechanical linkage 58 to move the ratcheting mechanism 46. This, in turn, moves the plunger 25 one unit toward the needle receiving end 28 of the barrel 26 and expels fluidic material 32. Piston 60 may be axially sealed within the chamber 72 by an o-ring 78 surrounding the piston. Of course, the biased position of the piston 60 is reversed in the aspiration apparatus embodiment of the present invention.

One significant advantage of the present invention over the prior art is that the mechanical linkage 58 used to move the ratcheting mechanism 46 permits the digital fluid delivery and aspiration apparatus 20 to operate at much lower pressure. Thus, the pneumatic air supply 75 need only deliver around 10 psi of air pressure whereas existing systems typically require around 40 psi. The amount of pressure of the compressed air 74 that the apparatus 20 requires depends on many variables and the pressure levels of the compressed air 74 described herein, while the preferred levels, are not the only pressure levels with which the present invention may be practiced.

The pneumatic air supply 75 (shown schematically in FIG. 16) may be similar to the ones disclosed in U.S. Pat. Nos. 5,354,268 and 5,520,652 or any of the many similar devices capable of providing the required air waveform. Electric power is provided to the pneumatic air supply 75 via a cable 83. A compressor 85 generates compressed air or, more broadly, pneumatic power and provides the pneumatic power to the digital fluid delivery and aspiration apparatus 20 through the air tube 76. The pneumatic air supply 75 forms pressure pulses (FIG. 15) at a rate and strength determined by the operator. The operator can control the frequency, amplitude, and shape (e.g., square, sinusoidal, triangular) of the waveform by adjusting controls 84 of the pneumatic air supply 75. The number or amount of pulses delivered to the apparatus 20 may be controlled using a foot pedal 86 or other control.

Several benefits, including reduced damage to tissue surrounding an injection site, arise from the use of an improved waveform 88 (FIG. 15) from the pneumatic air supply 75. The waveform 88 has a small, initial jump to a low pressure 89 to overcome friction and stiction in the apparatus 20. Beyond the friction and stiction level, the pressure is increased linearly along slope 90 and results in a substantially constant speed movement of the plunger 25 toward the needle receiving end 28 of the barrel 26 because of the linear increase in the counter force being provided by the spring compression. This constant speed of the plunger 25 substantially decreases the amount of tissue damage that may occur near the injection site. When the pressure reaches a maximum level 92, approximately 10 psi, the delivery of pneumatic power is ended, quickly stopping the motion of the plunger 25.

Unlike the prior art devices which have a piston displacement v. time curve substantially as shown in FIG. 13, the present invention (FIG. 14) has only a small jump 100 as frictional forces are overcome and then has a substantially linear acceleration to the point of maximum displacement 102. While in the prior art devices the initial jump to overcome system friction may be as much as 75% of the total motion of the plunger, the small jump 100 of the plunger in the present invention is a substantially minimal part of the total plunger motion. This reduced initial jump provides a significant decrease in the jetting of fluid and reduces the risk of tissue damage near the surgical site.

In operation as a fluid delivery apparatus, the surgeon using the digital fluid delivery and aspiration apparatus 20 connects the housing 24 to the pneumatic air supply 75 by attaching the air tube 76 to the tubing barb 75 leading into the chamber 72. The surgeon then positions the plunger 25 within the barrel 26 such that the fluidic material engaging head 34 is at the needle receiving end 28 of the barrel 26 and orients the flat faces 42 of the shaft 36 toward pawls 47 and 65 so that the plunger 25 may be freely moved along the length of the barrel 26 by manipulating the manual plunger control 38. The surgeon then draws fluidic material 32 into the barrel 26 by drawing the fluidic material engaging head 34 toward the plunger receiving end 30 of the barrel 26 until the desired amount of fluidic material 32 is in the barrel 26 of the syringe 22. When the syringe 22 is properly filled with fluidic material 32, the operator then orients the curved faces 40 of the shaft 36 to engage the pawls 47 and 65. The digital injector 20 is now ready to deliver the fluidic material 32 into the patient's tissue.

Referring now to FIGS. 11 and 12, when the syringe 22 is positioned to direct the fluidic material 32 to the proper location, the operator activates the pneumatic air supply 75 which provides compressed air 74 to the digital injector 20 in a pulse train substantially as shown in FIG. 15. As the pressure of the compressed air 74 is brought to maximum pressure 92, the piston 60 within the chamber 72 in the housing 24 is forced to move against the bias of the spring 73. This movement of the piston 60 causes the mechanical linkage 58, lever arm 66 in the preferred embodiment, to move the pawls 65 a discrete distance. The pawls 65 engage the teeth 44 on the shaft 36 of the plunger 25. Thus, the movement of the pawls 65 causes the plunger 25 to move a discrete distance toward the needle receiving end 28 of the barrel 26 thereby forcing fluidic material 32 out of the syringe 22. When the pneumatic air supply 71 reduces the pressure of the compressed air 74, the piston 60 is returned to its original position by the bias of the spring 73. As the piston 60 returns, a corresponding movement of the mechanical linkage 58 and the ratcheting mechanism 46 occurs. The shaft 36 is held in place by pawls 47 engaging the teeth 44. This prevents fluidic material 32 or other substances from being drawn into the syringe 22 as the pawls 65 ratchet over the teeth 44 to their new position. The cycle is complete and the digital fluid delivery and aspiration apparatus 20 is prepared to receive the next pulse of compressed air 74 from the pneumatic air supply 75 and to deliver the next discrete dose of fluidic material 32 to the injection site. With each cycling of the pressure of compressed air 74 delivered to the apparatus 20, a discrete amount of fluidic material 32 is delivered to the injection site.

The operation of the apparatus 20 as an aspiration apparatus is very similar, although opposite, to its operation as a fluid delivery apparatus. In the aspiration apparatus embodiment, each cycling of the pressure of compressed air 74 causes a discrete amount of fluidic material 32 to be drawn into the barrel 26 of the syringe 22. As should be evident to one of skill in the art, the operation of ratcheting mechanism 46 is opposite of that of the fluid delivery embodiment of the invention.

Figures 16, 17:
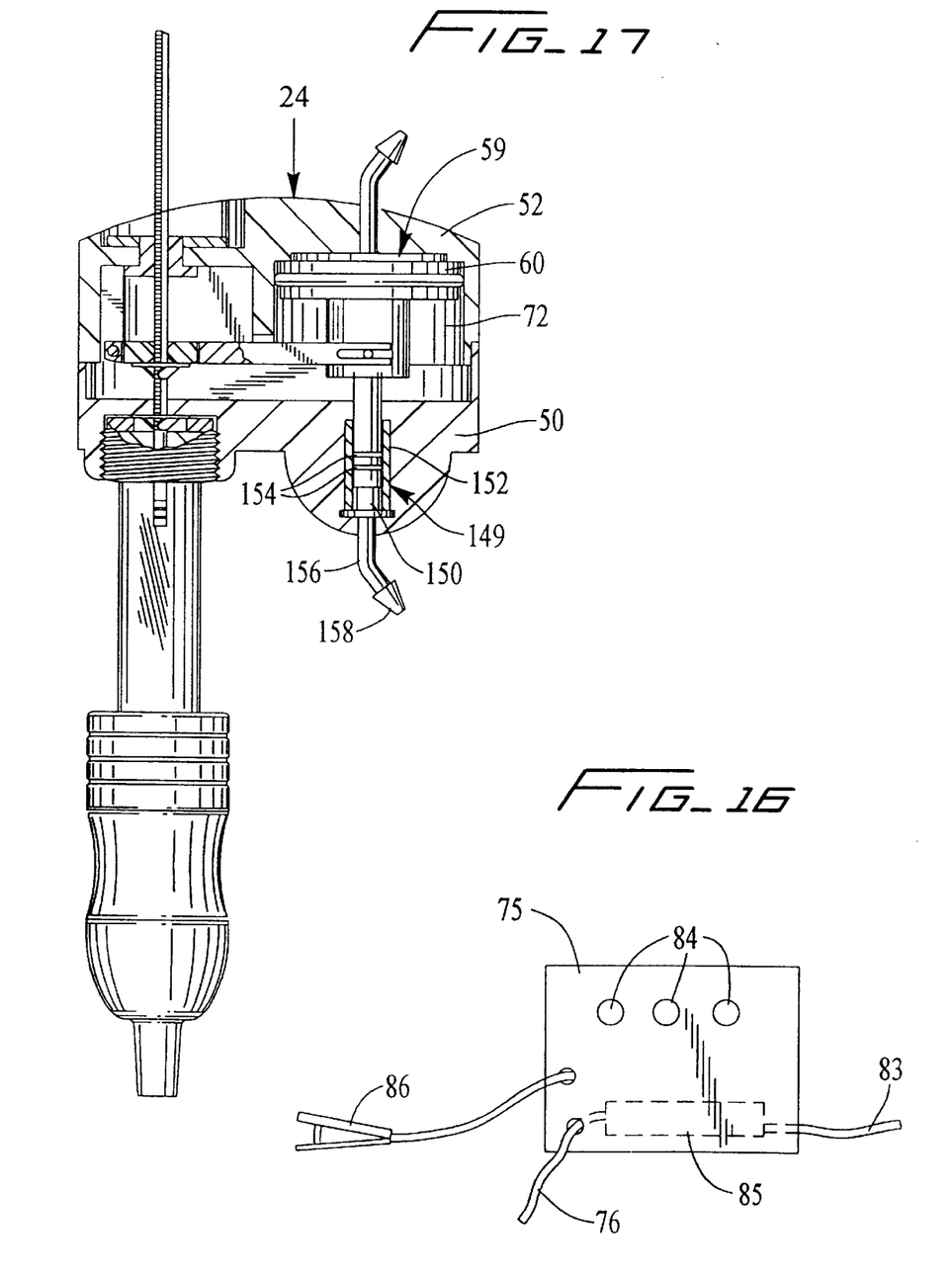
FIG. 16 is a schematic diagram of a pneumatic power supply that can be used to provide pneumatic pressure to apparatus constructed according to the present invention.
FIG. 17 is a side elevational view, shown partially in cross-section, of a digital fluid delivery and aspiration apparatus with a mechanical de-amplifier, constructed according to an alternative embodiment of the present invention.

FIG. 17 shows one alternative embodiment of a digital fluid delivery and aspiration apparatus 20 in accordance with the present invention. In this embodiment, a second fluid power actuator 149 is used instead of the spring 73 to bias the piston 60 toward the end of the chamber 72 formed by the cap 52. The second fluid power actuator 149 is formed by a second chamber 152 located in the base 50 of the housing 24, and includes a second piston 150. The second chamber 152 should be dimensioned such that the second piston 150 substantially sealably slides within the second chamber 152. The sealing interface may be effectuated by using second o-rings 154 around the second piston 150. The second piston 150 is biased toward the cap 52 by pneumatic or hydraulic pressure introduced into the second chamber 152 through a second air tube 156 and second hollow tubing barb 158. Of course, the pneumatic air supply 75 used with this embodiment of the invention must be able to control the pressure of the pneumatic or hydraulic fluid provided to the second chamber 152.

Figures 18, 19, 20, 21:
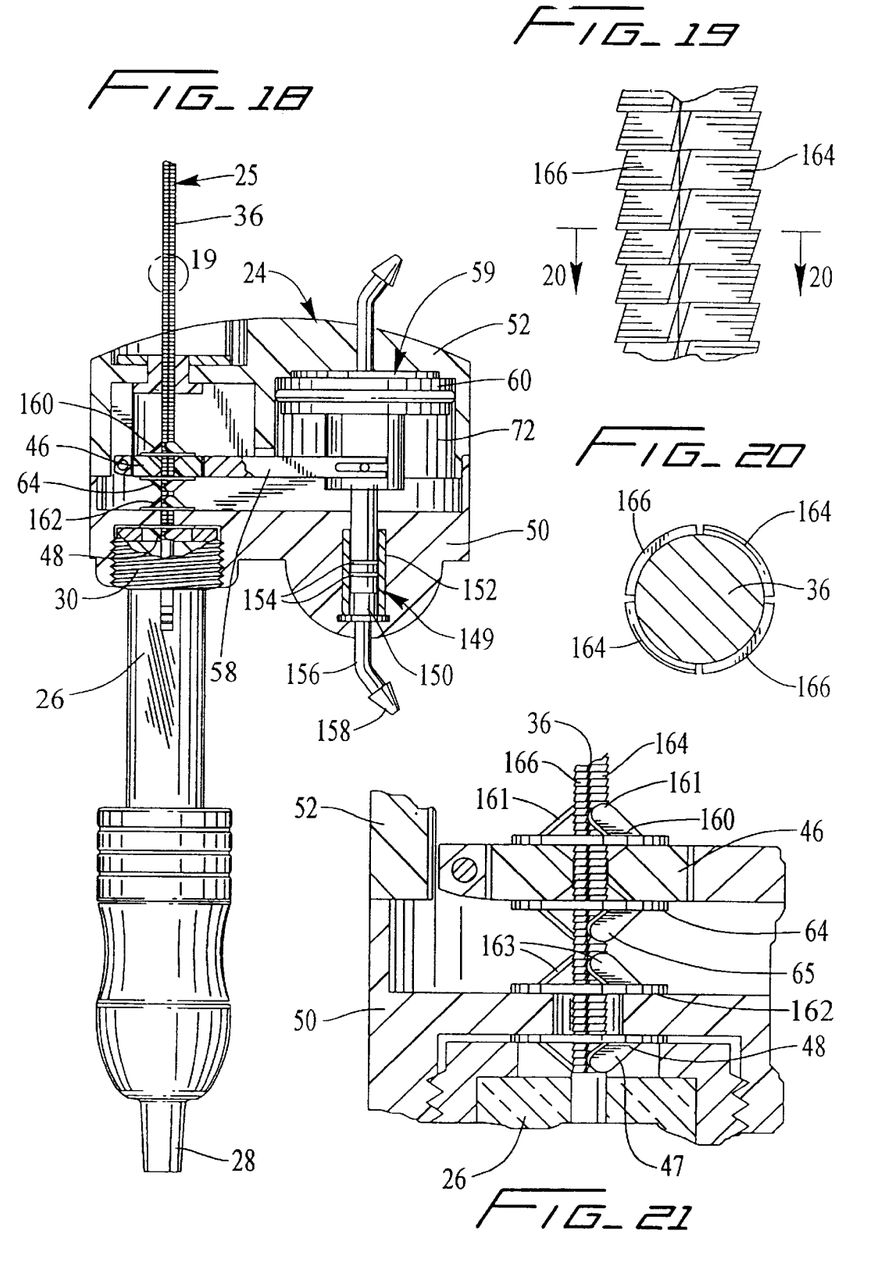
FIG. 18 is a side elevational view, partially in cross-section, of a digital fluid delivery and aspiration apparatus with a mechanical de-amplifier, constructed according to another alternative embodiment of the present invention, this apparatus capable of both irrigation and aspiration.
FIG. 19 is an enlarged detail view of the shaft of the plunger used in accordance with the embodiment of the invention in FIG. 18 taken generally from the circle 19 in FIG. 18.
FIG. 20 is a cross-sectional view of the shaft taken generally along the line 20—20 in FIG. 19.
FIG. 21 is a side elevational view, showing additional detail of the ratcheting mechanism used in accordance with the embodiment of the invention shown in FIG. 18.

FIGS. 18–21 show another alternative embodiment of a digital delivery and aspiration apparatus 20 in accordance with the present invention. In this embodiment, both fluid delivery ("irrigation") and aspiration activities may be performed by the same device. As with the embodiment shown in FIG. 17, the piston 60 is preferably biased toward the cap 52 of the housing 24 using a second fluid power actuator 149, including a second piston 150 located in the base 50 of the housing 24, although a spring 73 may again be used to provide the necessary bias. Again, the pneumatic air supply 75 used with this embodiment must be able to control the pressure of the pneumatic or hydraulic fluid provided to the second chamber 152 if a second piston 150 is used to bias the piston 60. As shown in FIG. 18 and in detail in FIG. 21, in this embodiment, a second ratchet spring 160, with integrated pawls 161, and second leaf spring 162, with integrated pawls 163, are used. Furthermore, the shaft 36 of the plunger 25 used in this embodiment has upward teeth 164 positioned side-by-side with downward teeth 166 (FIGS. 19 and 20) on its periphery and along part of the length of the shaft. The shaft 36 can then be rotated such that the upward teeth 164 engage the pawls 65 and 47, or such that the downward teeth 166 engage the pawls 161 and 163. When the shaft 36 is rotated such that the upward teeth 164 engage the pawls 65 and 47, operation of the apparatus 20 provides fluid delivery to the surgical site when the mechanical linkage 58 moves the ratcheting mechanism 46 as described above. When the shaft 36 is rotated such that the downward teeth 166 engage the pawls 161 and 163, operation of the apparatus 20 provides aspiration of the surgical site when the mechanical linkage 58 moves the ratcheting mechanism 46 as described above. The aspiration function is achieved because as the second ratchet spring 160 is caused by the mechanical linkage 58 to move toward the needle receiving end 28 of the barrel 26, the pawls 161 ratchet over the downward teeth 166. And as the mechanical linkage 58 causes the second ratchet spring 160 to move away from the needle receiving end 28 of the barrel 26, the second ratchet spring 160 engages the downward teeth 166 to cause the plunger 25 to move away from the needle receiving end 28 of the barrel 26. In this positioning of the shaft 36, the plunger 25 is prevented from moving toward the needle receiving end 28 of the barrel 26 by the pawls 163. Thus, digital control of the plunger 25 is achieved in either direction along the barrel 26. Of course, the barrel 26 must be filled and emptied of fluid by orienting the shaft 36 so that either the upward teeth 164 or the downward teeth 166 engage the shaft 36 when the mechanical linkage 58 is caused to move by activating the pneumatic air supply 75. The barrel 26 may also be manually filled by having smooth faces on the shaft 36 that do not engage any of the pawls 65, 47, 161 or 163.

Figure 22:
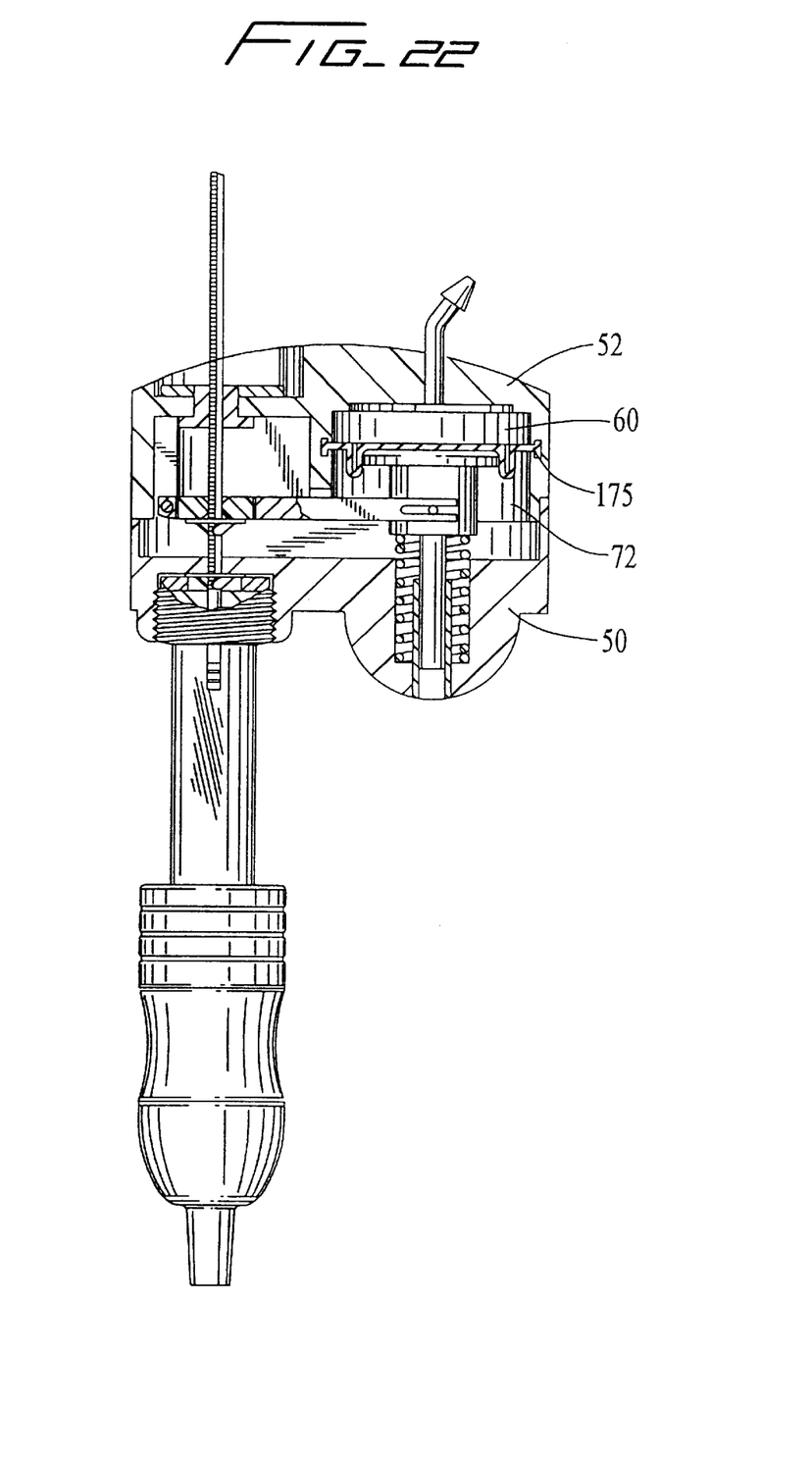
FIG. 22 is a side elevational view, shown partially in cross-section, of a digital fluid delivery and aspiration apparatus with a mechanical de-amplifier, constructed according to yet another alternative embodiment of the present invention.

In another embodiment of a digital fluid delivery and aspiration apparatus 20 in accordance with the present invention, shown in FIG. 22, the seal between the piston 60 and the chamber 72 is achieved by a rolling diaphragm 175 rather than an o-ring 78. In this embodiment, rolling diaphragm 175 unrolls as the piston 60 moves toward the base 50 end of the chamber 72 and rolls-up as the piston 60 moves toward the cap 52 end of the chamber 72. The rolling diaphragm 175 may be used in conjunction with any of the embodiments of the apparatus 20 disclosed herein or with any other embodiments that may be designed. A rolling diaphragm 175 may also be used to seal the second piston 150 within the second chamber 152. Of course, other means for sealing the engagement between the piston 60 and the chamber 72 and the second piston 150 and the second chamber 152 may also be used.

The various parts and components of the present invention may be made from a wide variety of materials. The materials are preferably corrosion resistant and autoclavable. Such materials include stainless steel, aluminum, glass, and polysulfone, or other plastics. Also, it should be recognized by one of skill in the art of the invention that while a pneumatically driven piston is the preferred embodiment, hydraulically driven pistons may be used.

As illustrated by the foregoing description and shown in the FIGS., the present invention is more suitable as a pneumatically controlled fluid delivery and aspiration apparatus than are existing devices. The present invention overcomes the limitations and disadvantages of existing devices by utilizing an effective design of a digital fluid delivery and aspiration apparatus with mechanical de-amplification that can operate at much lower pressure than existing devices, substantially reduces the amount of jetting of fluidic material from the open end of the syringe, and allows more precise control of the rate and volume of flow of fluidic material to and from the syringe.

Although the invention has been herein shown and described in what is perceived to be the most practical and preferred embodiment, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims.

What is claimed is:

1. A method of delivering fluidic material into a surgical site or aspirating fluidic material from a surgical site, the method comprising the steps of:

providing a plurality of pulses of air to a surgical apparatus, said apparatus having a plunger capable of forcing fluidic material from said apparatus and drawing fluidic material into said apparatus;

moving a piston housed within said apparatus in response to each of said plurality of pulses;

interrelating movement of said plunger to movement of said piston; and de-amplifying movement of said piston such that when said piston moves a distance, said plunger moves a shorter distance.

2. A device for aspirating discrete doses of fluidic material from tissue, the device comprising:

a housing having an aperture and containing a piston, said piston capable of being moved by a force;

a syringe having a needle receiving end, a plunger receiving end, and a hollow barrel between said needle receiving end and said plunger receiving end, said plunger receiving end of said syringe attached to said housing at said aperture;

a plunger having a periphery and a length; said plunger having a teeth on at least a portion of said periphery for at least a portion of said length, said plunger capable of passing through said aperture in said housing and said plunger receiving end of said barrel of said syringe;

a ratcheting mechanism within said housing; said ratcheting mechanism capable of engaging said teeth of said plunger such that when said ratcheting mechanism moves within said housing away from said syringe, said plunger is caused to move within said barrel away from said needle receiving end of said syringe, said ratcheting mechanism capable of disengaging said teeth of said plunger such that when said ratcheting mechanism moves within said housing toward said syringe, said plunger is not caused to move within said barrel; and a mechanical linkage interrelating movement of said piston to said ratcheting mechanism such that when said piston moves a distance, said ratcheting mechanism moves a shorter distance and such that said force moving said piston is translated into a greater force provided to move said ratcheting mechanism.

3. The device of claim 2 wherein:

said mechanical linkage further comprises a lever arm and a fulcrum on which the lever arm acts; said lever arm pivotably attached to said ratcheting mechanism at a ratchet pivot point; said lever arm pivotably attached to said piston at a piston pivot point;

said lever arm is capable of interrelating movement of said piston pivot point to movement of said ratchet pivot point such that when said piston pivot point moves a distance, said ratchet pivot point moves a shorter distance; and said lever arm is capable of translating a force applied at said piston pivot point to a greater force provided at said ratchet pivot point.

4. The device of claim 3 wherein:

said periphery of said plunger is formed by at least two faces;

at least one of said faces has teeth and at least one of said faces does not have teeth; and said plunger is capable of being rotated such that either said face having teeth or said face not having teeth can be oriented toward said ratcheting mechanism.

5. The device of claim 4 wherein said ratcheting mechanism further comprises:

a spring guide substantially surrounding said plunger; and a ratchet spring positioned by said spring guide and capable of engaging said portion of said plunger having teeth.

6. The device of claim 5 wherein said force is air pressure capable of overcoming a resistance force created by friction within said device and a spring biasing said piston against said air pressure.

7. The device of claim 6 further comprising a pneumatic air supply capable of providing a plurality of pulses of said air pressure at pressures above an ambient level; each of said plurality of pulses having a waveform wherein:

said air pressure is introduced to said device at a pressure sufficient to overcome friction within said device;

said air pressure is then increased to accelerate movement of said piston; and upon reaching a maximum pressure, said air pressure is reduced to said ambient level.

8. A device for aspirating discrete doses of fluidic material from tissue, the device comprising:

a housing having an aperture and containing a piston, said piston capable of being moved by compressed air;

a syringe having a needle receiving end, a plunger receiving end, and a hollow barrel between said needle receiving end and said plunger receiving end, said plunger receiving end of said syringe attached to said housing at said aperture;

a plunger having a periphery and a length, said plunger having teeth on a portion of said periphery for a portion of said length, said plunger capable of passing through said aperture in said housing and said barrel of said syringe;

a ratcheting mechanism within said housing, said ratcheting mechanism capable of engaging said teeth such that when said ratcheting mechanism moves within said housing away from said syringe, said plunger is caused to move within said barrel away from said needle receiving end of said syringe, said ratcheting mechanism capable of disengaging said teeth such that when said ratcheting mechanism moves within said housing toward from said syringe, said plunger does not move within said barrel toward said syringe; and a mechanical linkage interrelating movement of said piston to said ratcheting mechanism such that when said piston moves a distance, said ratcheting mechanism moves a shorter distance.

9. The device of claim 8 wherein:

said air pressure is capable of overcoming a resistance force created by friction within said device and a spring biased to position said piston against said air pressure; and said air pressure is provided to said device by a pneumatic air supply.

10. The device of claim 9 wherein said pneumatic air supply is capable of providing a plurality of pulses of said air pressure at pressures above an ambient level; each of said plurality of pulses having a waveform wherein:

said air pressure is introduced to said device at a pressure sufficient to overcome said friction within said device;

said air pressure is then increased to accelerate movement of said piston; and upon reaching a maximum pressure, said air pressure is reduced to said ambient level.

11. A device for delivering discrete doses of fluidic material into tissue and aspirating discrete doses of fluidic material from tissue, the device comprising:

a housing having an aperture and containing a piston, said piston capable of being moved by a force;

a syringe having a needle receiving end, a plunger receiving end, and a hollow barrel between said needle receiving end and said plunger receiving end, said plunger receiving end attached to said housing at said aperture;

a plunger having a periphery and a length, said plunger having upward teeth on at least a portion of said periphery for at least a portion of said length, said plunger having downward teeth on at least a portion of said periphery for at least a portion of said length, said plunger capable of passing through said aperture in said housing and said plunger receiving end of said barrel of said syringe;

a ratcheting mechanism within said housing, said ratcheting mechanism capable of selectively engaging either said upward teeth or said downward teeth such that when said ratcheting mechanism engages said upward teeth and said ratcheting mechanism moves within said housing toward said syringe, said plunger is caused to move within said barrel toward said needle receiving end of said syringe, and such that when said ratcheting mechanism engages said downward teeth and said ratcheting mechanism moves within said housing away from said syringe, said plunger is caused to move within said barrel away from said needle receiving end of said syringe; and a mechanical linkage interrelating movement of said piston to said ratcheting mechanism such that when said piston moves a distance, said ratcheting mechanism moves a related distance and such that said force moving said piston is translated into a related force provided to move said ratcheting mechanism.

12. The device of claim 11 wherein:

said mechanical linkage further comprises a lever arm and a fulcrum on which said lever arm acts, said lever arm pivotably attached to said ratcheting mechanism at a ratchet pivot point, said lever arm pivotably attached to said piston at a piston pivot point;

said lever arm is capable of interrelating movement of said piston pivot point to movement of said ratchet pivot point such that when said piston pivot point moves a distance, said ratchet pivot point moves a shorter distance; and said lever arm is capable of translating a force applied at said piston pivot point to a greater force provided at said ratchet pivot points.

13. The device of claim 12 wherein:

said periphery of said plunger is formed by a plurality of faces;

at least one of said faces has upward teeth;

at least one of said faces has downward teeth; and said plunger is capable of being rotated such that said face having upward teeth or said face having downward teeth can be selectively oriented to engage with said ratcheting mechanism.

* * * * *